(12) United States Patent  (10) Patent No.: US 8,006,540 B2
Degli Esposti et al.  (45) Date of Patent: Aug. 30, 2011

(54) AUTOMATIC SOLID-PHASE MICROEXTRACTION SAMPLING APPARATUS

(76) Inventors: Filippo Degli Esposti, Prato (IT); Vittorio Dugheri, Larciano (IT)

( * ) Notice: Subject to any disclaimer, the term of this patent is extended or adjusted under 35 U.S.C. 154(b) by 573 days.

(21) Appl. No.: 11/992,265

(22) PCT Filed: Sep. 6, 2006

(86) PCT No.: PCT/IT2006/000642
§ 371 (c)(1), (2), (4) Date: Mar. 17, 2008

(87) PCT Pub. No.: WO2007/032039
PCT Pub. Date: Mar. 22, 2007

(65) Prior Publication Data
US 2009/0260456 A1    Oct. 22, 2009

(30) Foreign Application Priority Data
Sep. 16, 2005 (IT) ............... FI2005A0194

(51) Int. Cl.
*G01N 1/28* (2006.01)
*G01N 30/00* (2006.01)
(52) U.S. Cl. ............ 73/23.41; 73/61.52; 73/61.55; 422/69; 422/70; 422/507; 436/161
(58) Field of Classification Search ............ 73/23.35, 73/23.41, 61.52, 61.55
See application file for complete search history.

(56) References Cited

U.S. PATENT DOCUMENTS

| 5,693,228 A * | 12/1997 | Koehler et al. ............ 210/656 |
| 7,178,414 B1 * | 2/2007 | Kokosa ............ 73/863.32 |
| 2004/0025302 A1 | 2/2004 | Alcaraz et al. |
| 2004/0241874 A1 * | 12/2004 | Abdel-Rehim ............ 436/177 |
| 2005/0011831 A1 | 1/2005 | Pawliszyn |

FOREIGN PATENT DOCUMENTS
GB    2401174 A    11/2004
* cited by examiner

*Primary Examiner* — Daniel S Larkin
(74) *Attorney, Agent, or Firm* — Pollack, P.C.

(57) ABSTRACT

An automatic solid-phase microextraction (SPME) sampling apparatus having a mobile sampler arm with a holder for a probe carrying a fiber 9 and an intermediate bracket for transferring the probe between a probe storage tray and the gas chromatograph injector. In the various probe handling stages, the probes are collected by a magnetic member attached to the end of the plunger in the holder, at the free end of the holder's body and at the lower end of the block for guiding the probe needle. The magnetic member interacts with a ferromagnetic connector attached to one end of the fiber and with a ferromagnetic flange attached to the end of the needle containing the fiber in order to place the probe on the transfer bracket or remove it therefrom. The apparatus can perform analyses on fibers that have already been exposed, extract analytes from samples, and subsequently transfer them for desorption in the gas chromatograph in a fully automatic way.

16 Claims, 7 Drawing Sheets

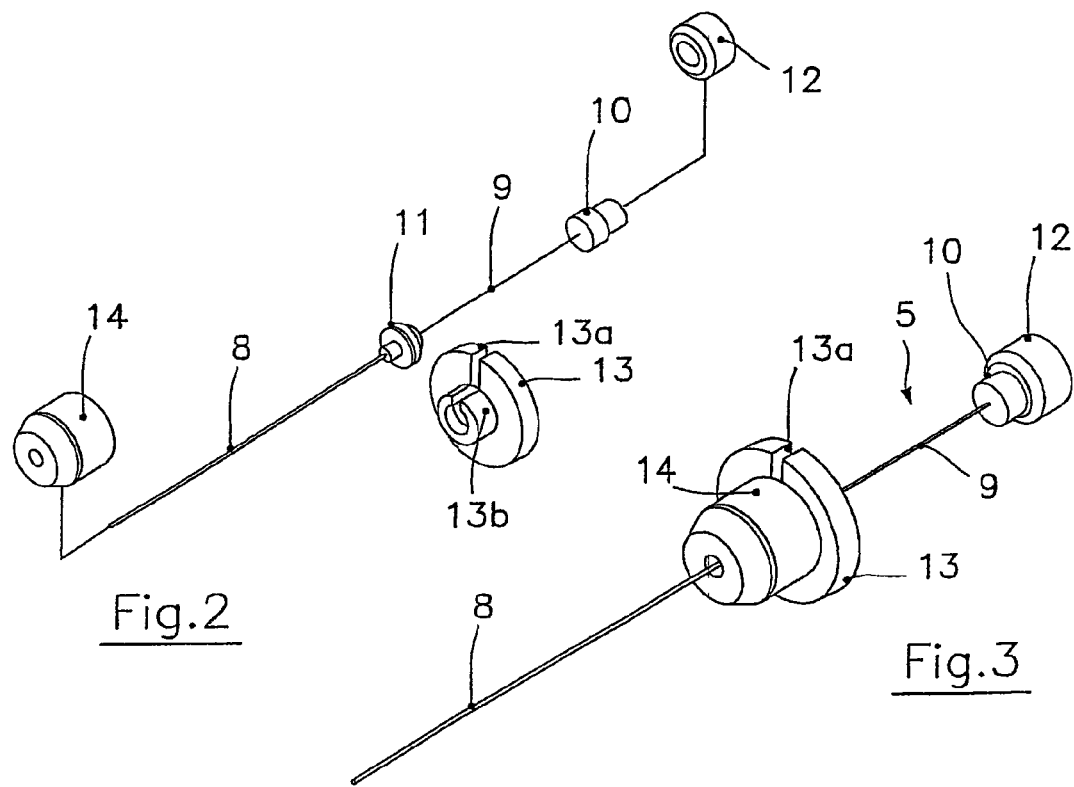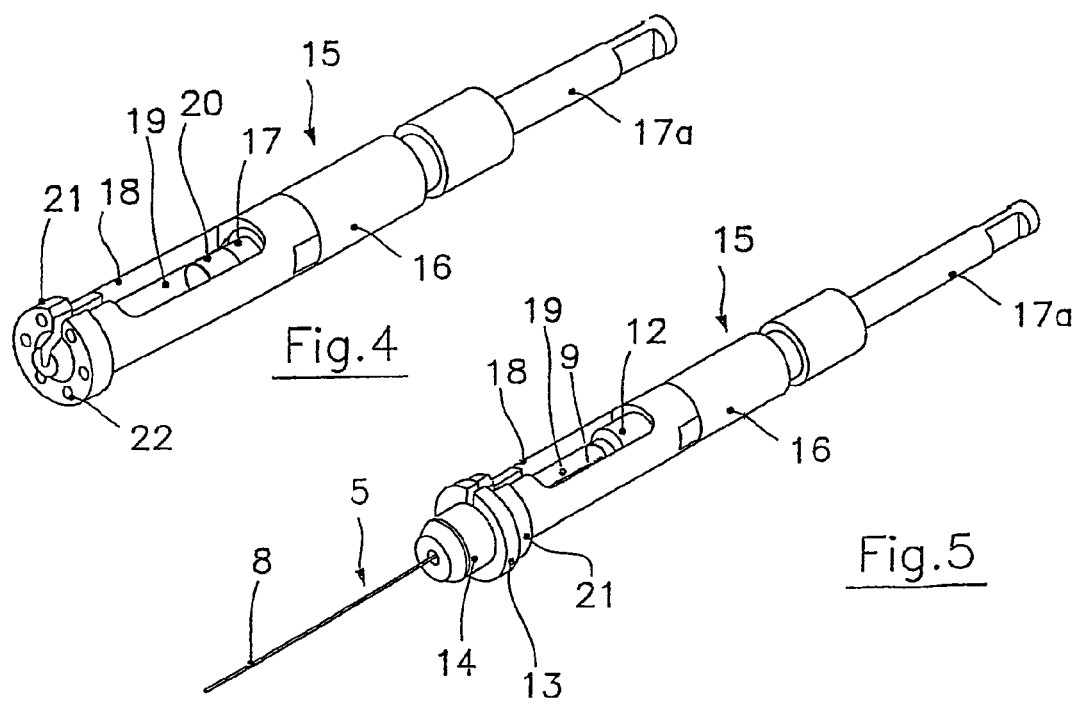

AUTOMATIC SOLID-PHASE MICROEXTRACTION SAMPLING APPARATUS

FIELD OF THE INVENTION

The present invention relates generally to analytical devices and, more particularly, to instrumentation for chemical analyses and the like.

BACKGROUND OF THE INVENTION

Solid-phase microextraction (or "SPME") is an analytical technique that uses a fluid polymer phase, a solid adsorbent, or a combination of the two, immobilized or coated on a fused silicon fiber. The coated fiber (hereinafter referred to as an "SPME fiber") is immersed in a liquid sample, or in the headspace above the sample, to absorb the analytes of interest, which are subsequently desorbed with the aid of heat in a gas chromatograph injector and thus transferred to a capillary column. The selectivity of this technique may be varied by changing the type or thickness of the phase coating on the fiber. This analytical method has found widespread use in various fields, being used for biological and environmental analyses, toxicology and in the agro-food sector.

An SPME unit essentially has two parts: (1) a probe comprising coated fused silicon fiber attached at one end to a plastic connector and housed slidingly in a needle such that the opposite end of the fiber may be exposed, and (2) a tubular, syringe-like container having a plunger threadably engaged with the connector. Sliding action of the plunger causes a larger or smaller portion of the fiber to extend from, or withdraw into, the needle. The analyte may be extracted either by exposing the coated portion of the fiber to the headspace of a test tube, immersing it in a fluid (e.g. water, milk, fruit juices, wines, etc.), or by exposing the fiber to air (for instance, in a working environment where the concentration of airborne pollutants is to be measured).

Generally speaking, there are three types of probe containers (hereinafter referred to as "holders") namely, holders for (i) manual analyses, (ii) field tests, and those for (iii) automatic samplers (or "autosamplers"). An autosampler is a well-known apparatus having a robotic arm that allows the user to automatically extract the analyte (i.e., conduct sampling) and inject it into the gas chromatograph. While conventional autosampplers have been found useful, the user must intervene each time a coated fiber must be replaced which, depending on the class of compounds being assayed, may require that fibers of different phases be immobilized. In such cases, the samples to be analyzed may be housed in test tubes inserted in suitable support plates that are accessible to the sampling head of the robotic arm.

Although SPME has been found beneficial, automation of the extraction/injection process is often limited because of the necessity that the user intervene each time the probe, installed on the autosampler arm, must be changed. There are, indeed, situations, when the probe has to be replaced after each injection in the gas chromatograph, making automated analysis unfeasible. Such is the case, for example, in determining levels of airborne pollutants as, during a given sampling campaign, technician collecting samples is likely to return to the laboratory with a large number of probes whose fibers have been exposed to the environment or are being monitored. In this type of analysis, the number of fibers depends on the number of sampling points chosen, and on the number of individuals working, in the area being monitored. Specifically, one or more probes may be attached to the workers' clothing to assess their exposure to airborne pollutants.

In environmental analyses, each SPME probe is effectively equivalent to a testtube that users of conventional arrangements must always change inside the holder before they can inject the sample into the gas chromatograph. Using When using holders currently available on the market, while SPME fibers can be used on some autosamplers, multiple fibers cannot be used simultaneously in a single working session unless the autosampler is stopped and an operator is on hand to change the probe. Moreover, where each fiber represents a selected sampling point, there is generally no difference—in terms of timesaving—between injecting the analyte through the port by hand or installing the fiber of the holder in the autosampler. Unfortuneately, if, for instance, there are two sets of samples on which two substances must be assayed, that require two different SPME fibers, then the first set of samples must be analyzed first, and, subsequently, the fiber changed before the second set of samples can be analyzed. Although this issue is already problematic with assays on liquid or biological samples, it becomes magnified during environmental sampling, when the absence of a fully automated procedure increases considerably the time necessary to perform the analyses.

OBJECTS AND SUMMARY OF THE INVENTION

Accordingly, it is an object of the present invention to provide an automatic sampling apparatus for use in solid-phase microextraction (SPME) that enables automatic replacement of SPME probes on an autosampler arm.

It is another object of the present invention to provide an automatic sampling apparatus for use in solid-phase microextraction that enables an SPME fiber on an autosampler arm to be changed such that it may be readily integratable in conventional sampling equipment, by simply adding selected components.

It is a further object of the present invention to provide an adapter kit with the components necessary for converting a conventional semiautomatic autosampler into a fully automatic apparatus according to the present invention.

It is yet another object of the present invention is to provide an SPME probe suitable for use in an automatic sampling apparatus for solid-phase microextraction.

According to one aspect of the present invention, there is provided an automatic solid-phase microextraction apparatus using a probe comprising a fiber arranged slidingly inside a needle such that the fiber may be exposed to an environment from which it can absorb an analyte of interest and in a gas chromatographic injector for desorption of the analyte. The apparatus comprises an arm movable according to a pre-established program, with a head carrying a substantially tubular holder with a chamber for the probe and a plunger in the holder for actuating the protrusion and withdrawal of at least a portion of the fiber. The apparatus also comprises a storage unit of test tubes containing samples to analyze and/or probes with already-exposed fibers. One end of the fiber in the probe mounts a connection element made of a selected ferromagnetic material and an end of the needle wherein the fiber is engaged has a ferromagnetic flange. In addition, the plunger in the holder has at least one magnet at the end interacting with the fiber, and one or more further magnets at a free end of the holder. The head comprises at least one guide block for slidingly housing the needle when the probe is engaged in the holder, the guide block being arranged underneath the free end of the holder and mounting at least one magnet at its lower end. Furthermore, there is provided an intermediate transfer bracket accessible to the mobile arm and suitable for vertically supporting one probe, and comprising a device for engaging a ferromagnetic connector on the fiber and the ferromagnetic flange on the needle. The head of the movable arm is suitable for collecting the probe according to a first collection mode, by bringing the end of the at least one guide block into engagement with the ferromagnetic connector on the fiber, or according to a second collection mode, by bringing the end of the plunger and the free end of the holder respectively into engagement with the connector on the fiber and the flange on the needle, whereby the probe is placed inside the chamber of the holder with the needle extending axially therefrom. The first collection mode is used to transfer the probe from the storage unit to the intermediate transfer bracket and vice versa, whereas the second collection mode is used to transfer the probe from the intermediate transfer bracket to the gas chromatograph injector or to the storage unit to absorb an analyte, as a result of corresponding movements of the mobile arm.

In accordance with another aspect of the present invention, a probe is provided for solid-phase microextraction. The probe comprises a fiber slidingly housed in a needle, wherein the fiber has a connector made of a selected ferromagnetic material at one end, and an end of the needle in which the fiber is engaged has a flange made of a selected ferromagnetic material.

According to a further aspect of the present invention, an adapter is provided for converting semi-automatic solid-phase microextraction sampling equipment to equipment that is fully automatic, m risin a fiber slidingly housed in a needle such that the fiber may be exposed in an environment, from which it can absorb an analyte of interest, and in a gas chromatograph injector for the desorption of the analyte. The adaptor has an adaptor cap made of a selected ferromagnetic material for attaching to a connector situated at an end of the fiber, the connector being made of a selected ferromagnetic material. The adaptor also has a flange made of a selected ferromagnetic material with a corresponding mounting sleeve for attachment to a spacer ring on an end of the needle. In addition, the adaptor includes a plurality of magnetic elements for attaching to the end of a plunger of a holder for the probe, to a free end of the holder, and to a free end of a guide block for slidingly housing the needle carried by a head of the mobile arm of the equipment. Furthermore, the adaptor is provided with an intermediate transfer bracket for vertically supporting a probe and comprising a device for engaging the ferromagnetic connector on the fiber and the ferromagnetic flange.

BRIEF DESCRIPTION OF THE DRAWINGS

A specific, illustrative automatic solid-phase microextraction (SPME) sampling apparatus, according to the present invention, is described below with reference to the accompanying drawings, in which:

FIGS. 2 and 3 show exploded and assembled perspective views, respectively, of a probe with an SPME fiber, in accordance with the present invention;

FIG. 4 is a perspective view of a holder for the probe with the SPME fiber shown in FIGS. 2 and 3;

FIG. 5 is a perspective view of the holder illustrated in FIG. 4 complete with the probe and SPME fiber;

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
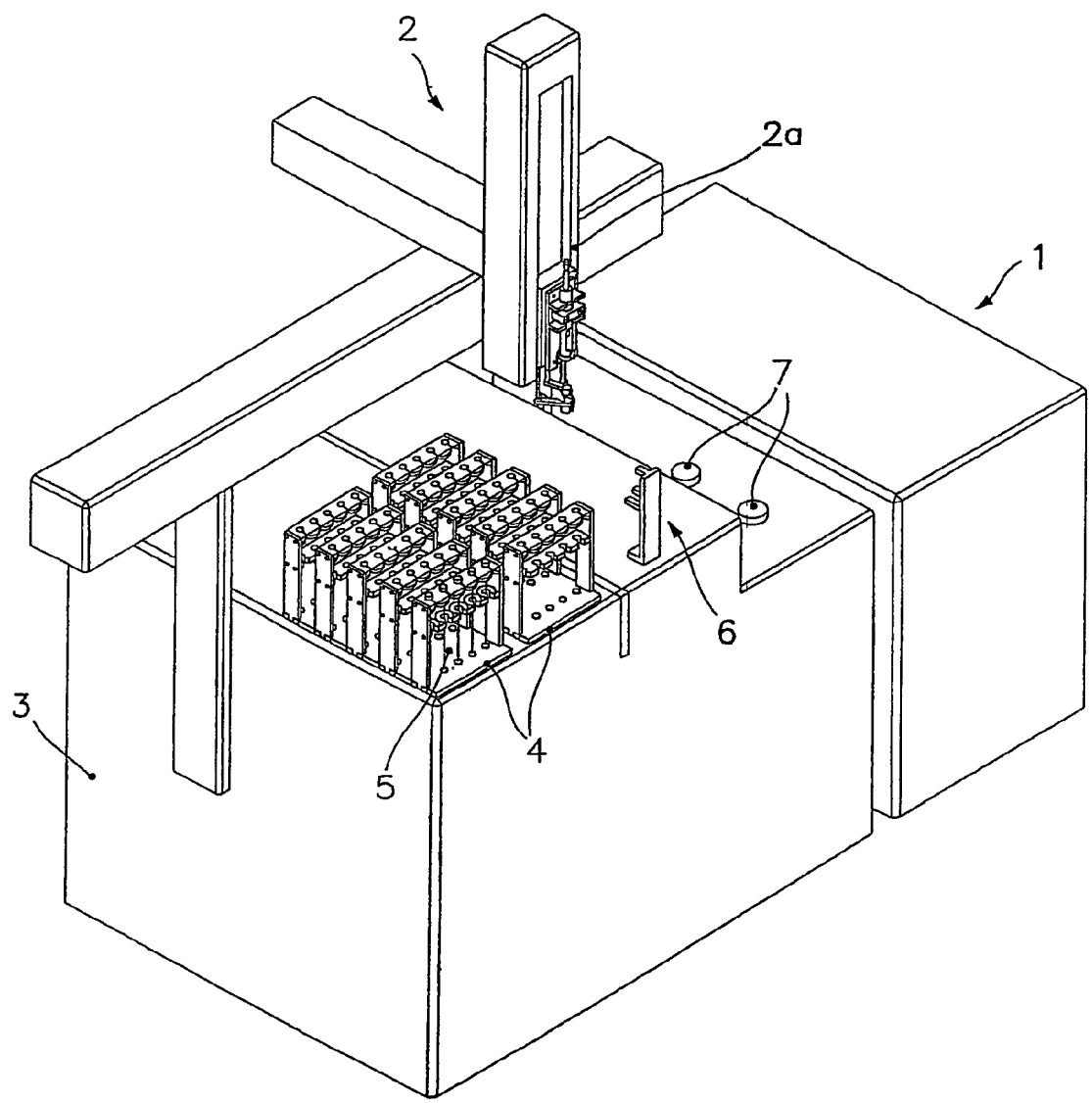
FIG. 1 is a perspective view of an automatic solid-phase microextraction sampling apparatus, according to one aspect of the present invention.

Referring now to the drawings and, more particularly, to FIGS. 1-11, there is shown generally a specific, illustrative automatic sold-phase microextraction or SPME sampling apparatus, according to various aspects of the present invention. In one embodiment, set forth generally in FIG. 1, the apparatus is shown in association with a detector for gas chromatographic analyses (a mass spectrometer, for example) 1. The apparatus comprises a robotic autosampler arm 2 supported by the gas chromatograph, on which one or more trays 4 for supporting probes 5 with SPME fibers are neatly arranged. These probes may, for instance, come from a campaign of environmental analyses and are ready for gas chromatographic analysis. Alongside the trays, a bracket 6 is provided for transferring the probes. The gas chromatographic apparatus also includes a plurality of injectors, e.g., two.

As shown in FIGS. 2 and 3, sampling probe according to one aspect of the present invention, comprises a conventional probe having a needle 8, that slidingly houses a solid-phas microextraction ("SPME") fiber 9. A plastic connector 10 is attached to one end of the fiber and—in conventional systems—is threadably engaged with the probe holder's plunger. A spacer ring 11, e.g., of brass, is likewise attached to an adjacent end of the needle. An adapter cap 12 constructed of a selected ferromagnetic material is preferably attached to connector 10, while a flange 13 also made of a selected ferromagnetic material is secured to spacer ring 11. In particular, flange 13 has a radial discontinuity 13a and a portion 13b that is threaded both internally and externally. To mount the flange on the spacer ring, the needle is passed through discontinuity 13a until it is coaxial with the flange, which is screwed onto the spacer ring by its threaded portion 13b until the two are juxtaposed. A mounting sleeve 14 is then threadably engaged with threaded portion 13b coaxially to the needle.

As shown in FIGS. 4 and 5, a holder 15 is provided of substantially conventional structure, suitable for attaching to head 2a of sampler arm 2 for carrying probe 5 with SPME fiber 9. The holder comprises a tubular body 16 for slidingly receiving a plunger 17, a stem 17a of which is connected to a moving device (not shown). Such moving devices are well-known to those skilled in the art and further description is considered unnecessary for illustration of the present invention. Tubular body 16 has a longitudinal window 18 affording access to a chamber 19 containing probe 5 during its movement, as shown in FIG. 5, so that needle 8 extends axially therefrom. In particular, a magnet 20 is attached to an end of plunger 17 inside chamber 19 (FIG. 4); likewise, a flange 21 carrying a circularly arranged row of magnetic elements 22 is joined to the free end of tubular body 16. Both flange 21 and the free end have a radial discontinuity allowing passage of the needle when the probe is placed inside the chamber (as shown in FIG. 5) or removed therefrom. In the position shown in FIG. 5, probe 5 is secured to the holder by the two magnetic connections comprising, on one side, adaptor cap 12, which becomes attached to magnet 20 situated at the end of plunger 17, and, on the other side, flange 13, which becomes attached to magnetic flange 21 situated at the free end of the tubular body.

Figure 6:
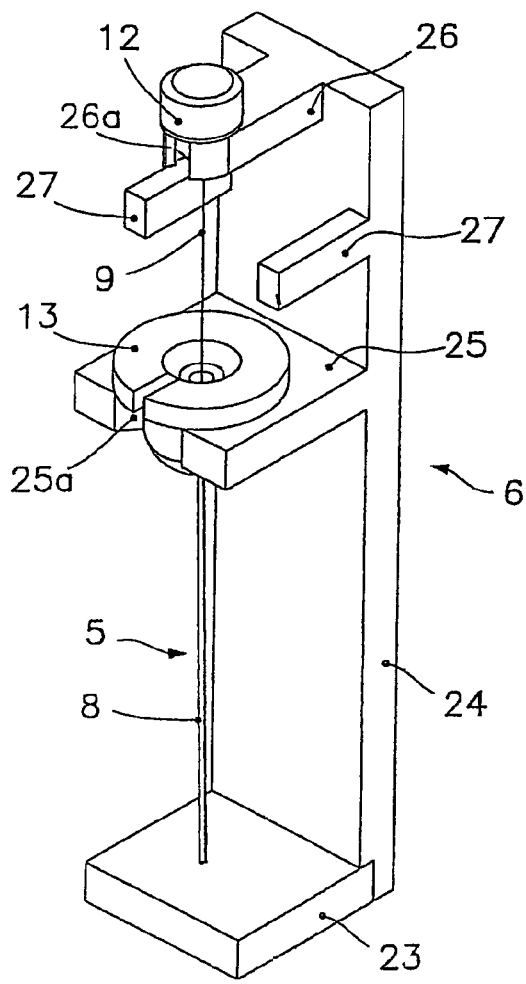
FIG. 6 is a perspective view of a transfer bracket with a probe containing an SPME fiber installed thereon, according to the present invention.

As best seen in FIG. 6, bracket 6 comprises a base 23, which may be secured to casing 3 of the apparatus, and an upright 24 rising from the base. First and second supporting plates 25 and 26, respectively, preferably extend from upright 24 over base 23, and are intended to engage adaptor cap 12 and flange 13 on probe 5 (carrying SPME fiber 9) in their respective seats 25a and 26a. Between first and second supporting plates 25 and 26, a pair of arms 27 also extend from upright 24, as set forth in more detail below.

Figure 7:
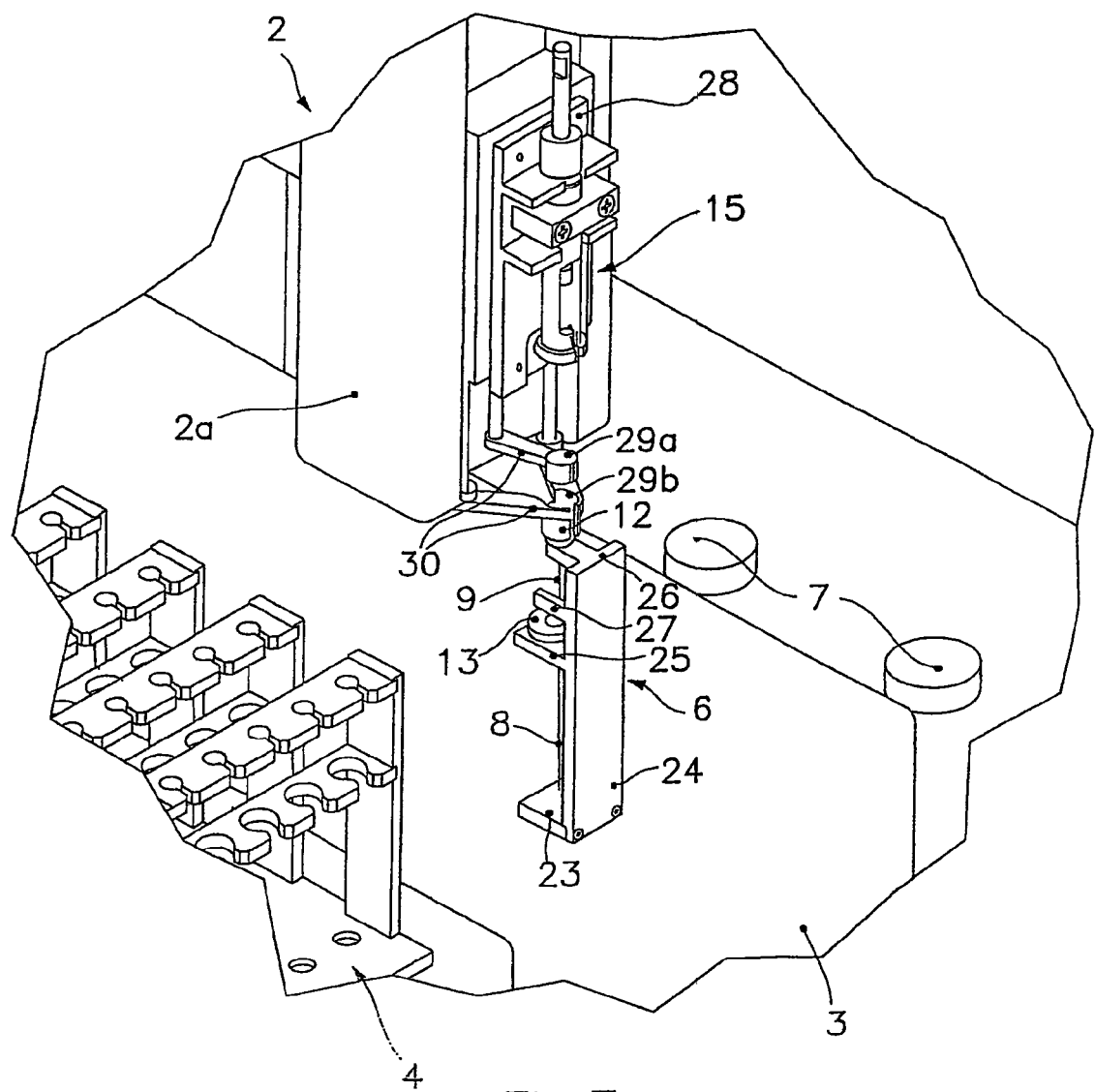
FIG. 7 shows positioning of a probe with an SPME fiber on a transfer station, in accordance with the present invention.
Figure 10:
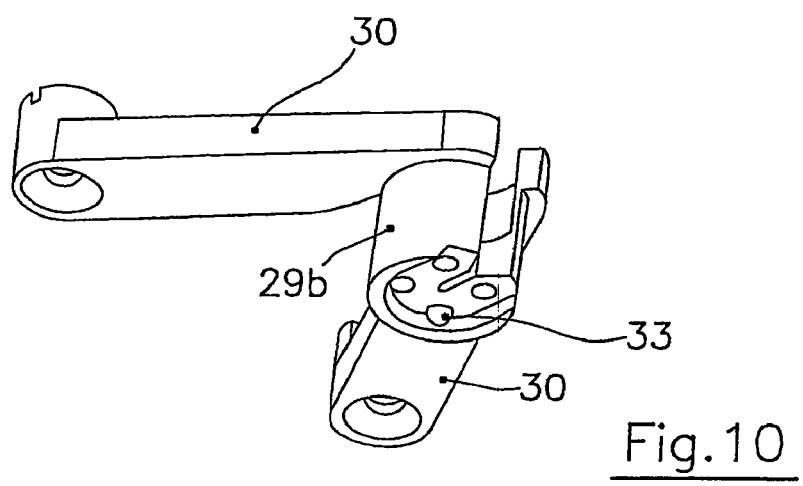
FIG. 10 is a reverse perspective view of a guide block on the head of the autosampler arm.
Figure 11:
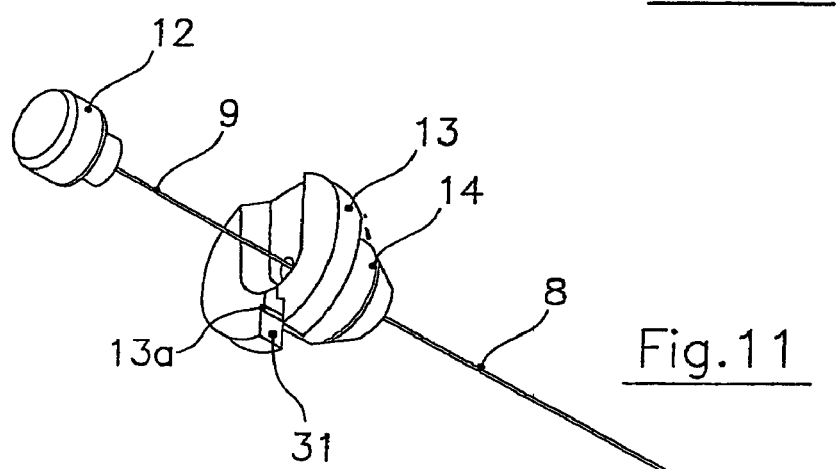
FIG. 11 is a perspective view of a probe with an SPME fiber, according to another aspect of the present invention.

As illustrated in FIG. 7, holder 15 is secured to head 2a of autosampler arm 2 in a substantially conventional manner, e.g., by a plate 28. Head 2a is also provided with two guide blocks 29a, 29b for guiding the needle of the probe, in alignment below holder plate 28 and supported by arms 30 extending from plate 28. Moreover, as shown in FIG. 10, the lower of the two guide blocks 29b carries a circularly arranged row of magnets 33 on its underside so that it can be magnetically coupled with adaptor cap 12 on SPME fiber 9.

Figure 8:
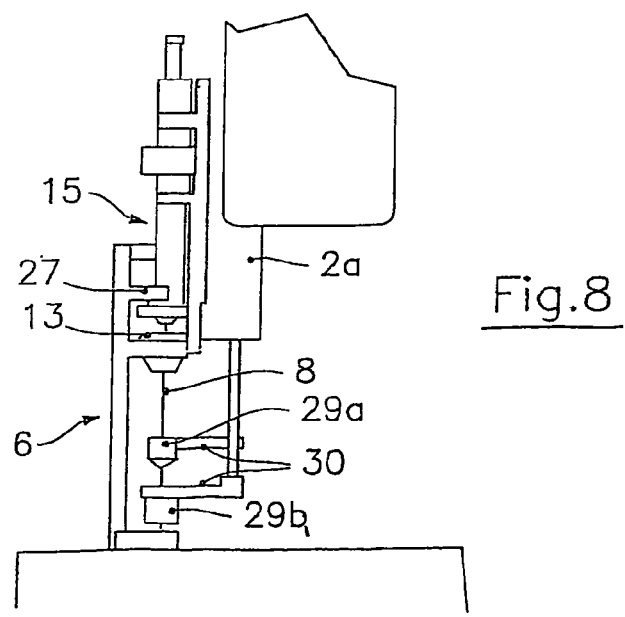
FIG. 8 is a side view of a method step when the probe with the SPME fiber is loaded from the transfer station shown in FIG. 7 on to the holder carried by the autosampler arm.
Figure 9:
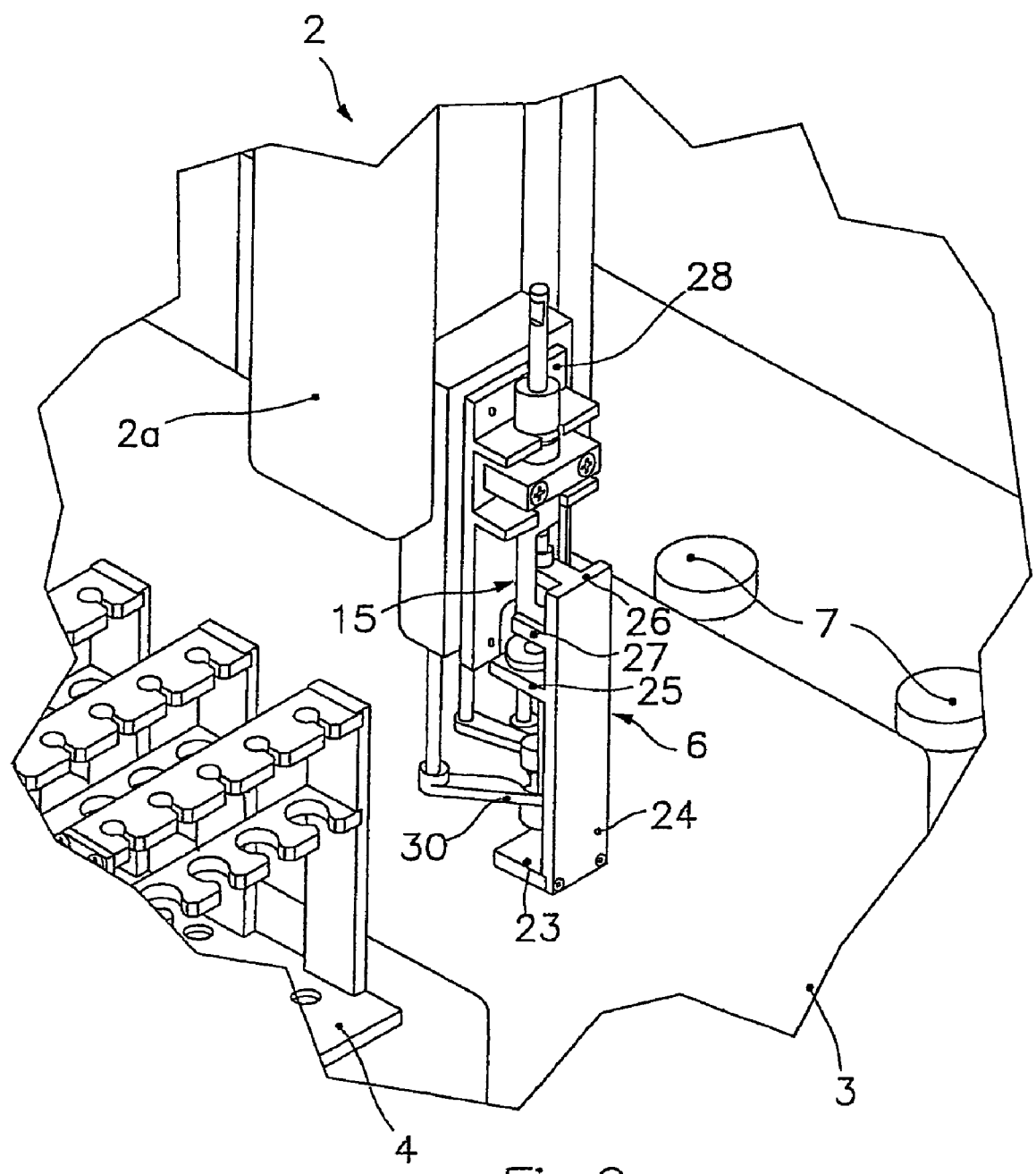
FIG. 9 is a perspective view of the step illustrated in FIG. 8.

In operation, as illustrated generally in FIGS. 7, 8 and 9 initially probes 5—for instance, as part of a campaign of environmental analyses—are placed vertically in suitable racks in tray 4, while head 2a of sampler arm 2 is in a stowed position, as shown in FIG. 1. Sampler arm 2 preferably utilizes Cartesian type movement controlled by a computer (not shown), which stores a map of the tray with the position of each probe, so that it can move into position over the probes on the tray and align guide blocks 29a, 29b over the required probe. A downward movement then begins until lower guide block 29b engages magnetically adaptor cap 12 of the probe. Consequently, the probe may be lifted from its seat in the tray and carried to transfer bracket 6, where it is placed with adaptor cap 12 and flange 13 resting on support plates 25 and 26, in seats 25a and 26a, respectively. The end of guide block 29b is separated from the adaptor cap by sliding guide block 29b longitudinally away from the transfer bracket. The adaptor cap is maintained in its seat by plastic connector 10 projecting therefrom, and then detached when block 29b is moved away from the transfer bracket and its magnets are no longer in contact with the cap.

Upon its separation from the probe, head 2a of the sampler arm moves downwardly so as to position window 18 of the holder into alignment with the adaptor cap. Subsequently, a forward sliding movement of the head displaces the holder towards upright 24 until the adaptor cap is inside chamber 19 in the holder, as shown in FIGS. 8 and 9.

Next, plunger 17 brings its magnetic end 20 into engagement with adaptor cap 12, which remains attached thereto, after which head 2a on the arm 2 moves such that its magnetic flange 21 comes into contact with flange 13 on the needle. In this manner, probe 5 becomes firmly attached to holder 15 and, can consequently, may be separated from the transfer bracket 6 and carried towards gas chromatograph injector 7, with which needle 8 ultimately becomes engages. At this stage, the needle also becomes engaged with guide blocks 29a, 29b to prevent it from being bent upon insertion in the injector.

Once needle 8 is inserted into injector 7, the process continues in the usual manner: fiber 9 in the needle is exposed so as to enable desorption of the substance being analyzed and, when a desired time has elapsed, the needle is withdrawn from the injector and the probe returned to transfer bracket 6, where it is repositioned as shown in FIG. 9. The probe is preferably detached by raising plunger 17 in the holder until magnet 20 is separated from adaptor cap 12 when it abuts the top of window 18. Next, the holder pulls the probe upwardly until flange 13 abuts arms 27 with sufficient force to overcome the magnetic force between magnetic flange 21 and flange 13, so that probe 5 drops freely down the transfer bracket until the adaptor cap and flange 13 engage their respective seats 25a and 26a in plates 25 and 26, respectively. The previously-described sample collection steps are then conducted in reverse order until the probe is restored to its seat in the tray and the autosampler arm 2 is ready to collect a new probe 5.

In general, there are two different ways or operating modes for a mobile sampler arm to collect a probe, in accordance with the present invention. In the first mode, the probe is connected to the head of the arm by its adapter cap 12, which cap is attached magnetically to a lower end of guide block 29b. This enables the probe to be positioned on transfer bracket 6 and detached therefrom. The second mode involves connecting the probe to holder 15 by adapter cap 12 and flange 13, which are attached magnetically to the end of plunger 17a and to the free end of holder body 16, respectively. This arrangement enables transfer of the probe from the transfer bracket to the holder, and its subsequent reinsertion in the bracket. Beneficially, passage of the probe from one collecting mode to the other, through movement of mobile arm 2 and use of transfer bracket 6, enables the procedure for analyzing a plurality of samples to be fully automated.

The apparatus, according to one aspect of the present invention, can be used advantageously not only to perform analyses using probes containing already exposed SPME fibers, but also for the directed extraction of analytes of interest from samples contained in test tubes placed in the tray and their subsequent desorption in the gas chromatograph. In this case, through a sequence that, in view of the disclosure above, would be apparent to one skilled in the art, head 2a of the autosampler arm (carrying a probe 5 that has yet to be exposed) is brought over a selected test tube in tray 4 and needle 8 inserted in the test tube, by sliding plunger 17 into holder 15. Again, the needle is engaged in guide blocks 29a, 29b to avoid risk of bending, due to the force exerted by the plunger on the needle during insertion in the testtube. Once the SPME fiber is exposed inside the testtube for a required time, it is withdrawn into the needle, which is removed from the testtube. The the probe is then transferred to the gas chromatograph injector, into which it is inserted and the desorption phase begins.

Advantageously, if the analytes to assay belong to different classes of compounds and, consequently, require fibers with different phases, the apparatus according to the invention can automatically fit an appropriate unexposed probe, collecting it from the tray 4 after depositing the previously-used probe. The changeover is made using transfer bracket 6 in the manner described above.

Figure 12:
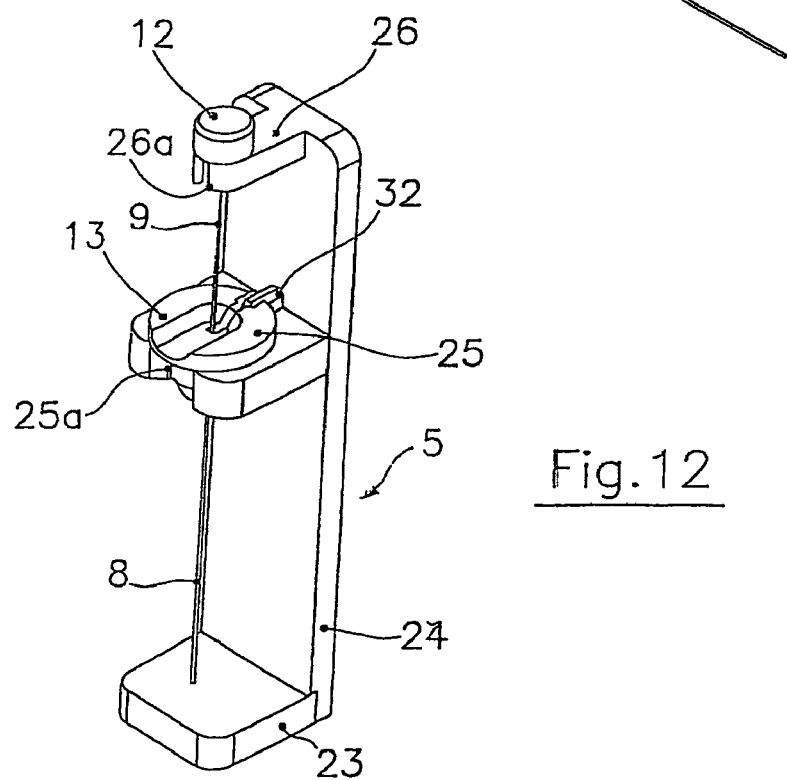
FIG. 12 is a perspective view of a transfer station suitable for use with the probe with the SPME fiber of FIG. 11, in accordance with a further aspect of the present invention.

Next, probe 5 is detached from flange 21 by a pair of arms 27 up against which the probe's flange 13 is biased until the force so developed exceeds the magnetic force between the latter and flange 21. According to an alternative embodiment, illustrated generally in FIGS. 11 and 12, probe 5 is detached from guide block 29b in the same manner, while flange 21 is separated from flange 13 by simple traction exerted by head 2a in an orthogonal direction away from needle 8. For this purpose, radial discontinuity 13a on flange 13, for inserting the needle, has a widened opening section 31. A corresponding reference tooth 32 is provided on plate 25 of transfer bracket 6 for engaging the widened opening section such that, while the probe is kept in a generally constant position on the transfer bracket, it can be detached by radial traction without risk of the probe sliding out. This is because flange 13 and the adapter cap abut one another laterally on their respective seats. Such solution also avoids the probe being positioned by dropping onto the transfer bracket, which could damage the probe.

Figure 13:
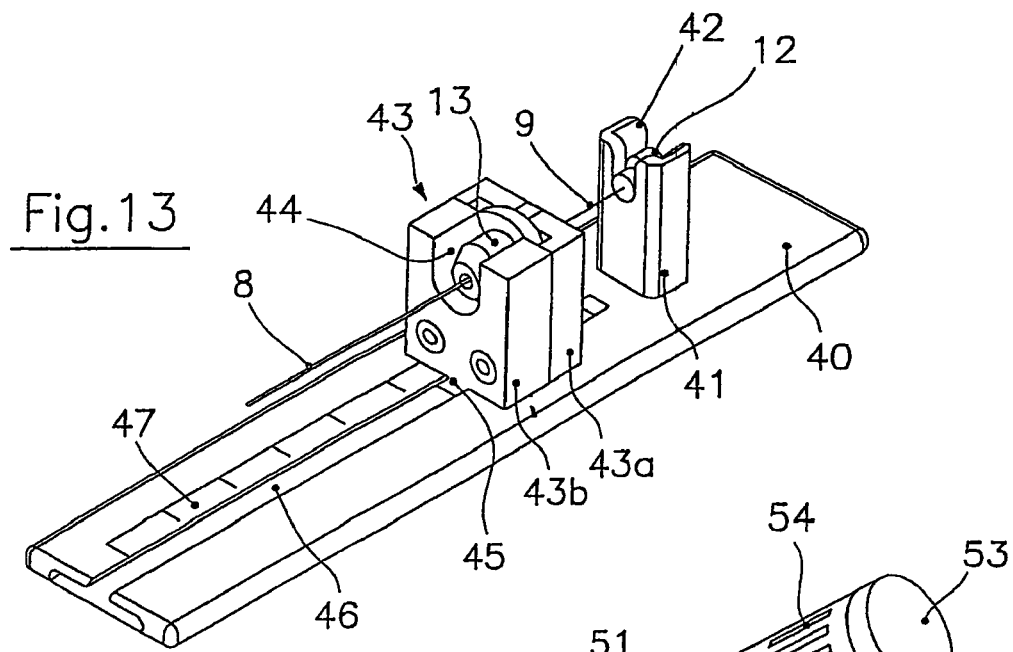
FIG. 13 is a perspective view of a device for calibrating a probe, according to one aspect of the present invention.

As shown in FIG. 13, a useful accessory or device is provided for the apparatus, according to yet another aspect of the present invention. The device is preferably used in calibrating the probe, i.e., for adjusting Z—a parameter representing the extent to which the fiber is withdrawn inside the needle. This parameter determines the extent of exposure of the fiber and the resulting sampling range. The device comprises a plate 40 with a first block 41 secured in a median longitudinal position, which has a first seat 42 shaped so as to retain adaptor cap 12 on the probe, and a second movable block 43 comprised of two coupled parts 43a and 43b that, between them, define a second seat 44 shaped so as to contain probe flange 13 and prevent it from sliding axially therein. At least one of the blocks has a T-shaped appendage 45 engaged with a slot 46 of corresponding shape formed longitudinally on plate 40. Once the probe is positioned on blocks 41 and 43 so that it lies generally parallel to the plate, with the adaptor cap and the flange 13 engaged in their respective seats 42 and 44, the block 43 is slidable relative to block 41 for achieving the required adjustment. As shown schematically in FIG. 13, a suitable scale 47 is provided on the plate 40, for reading the extent of the probe's withdrawal.

Figure 14:
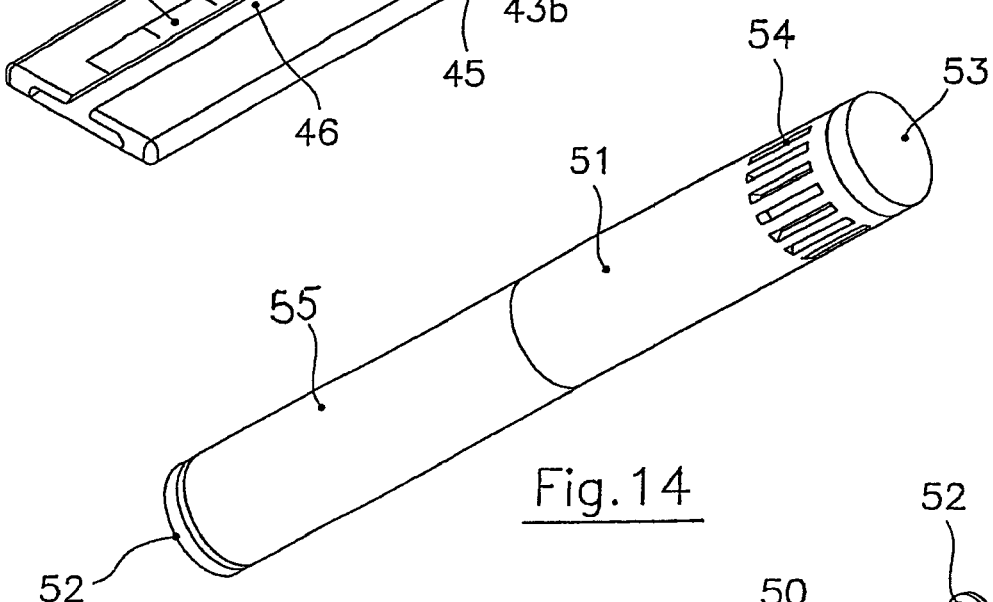
FIG. 14 is a perspective view of a protective container for the probe set forth in FIG. 13.
Figure 15:
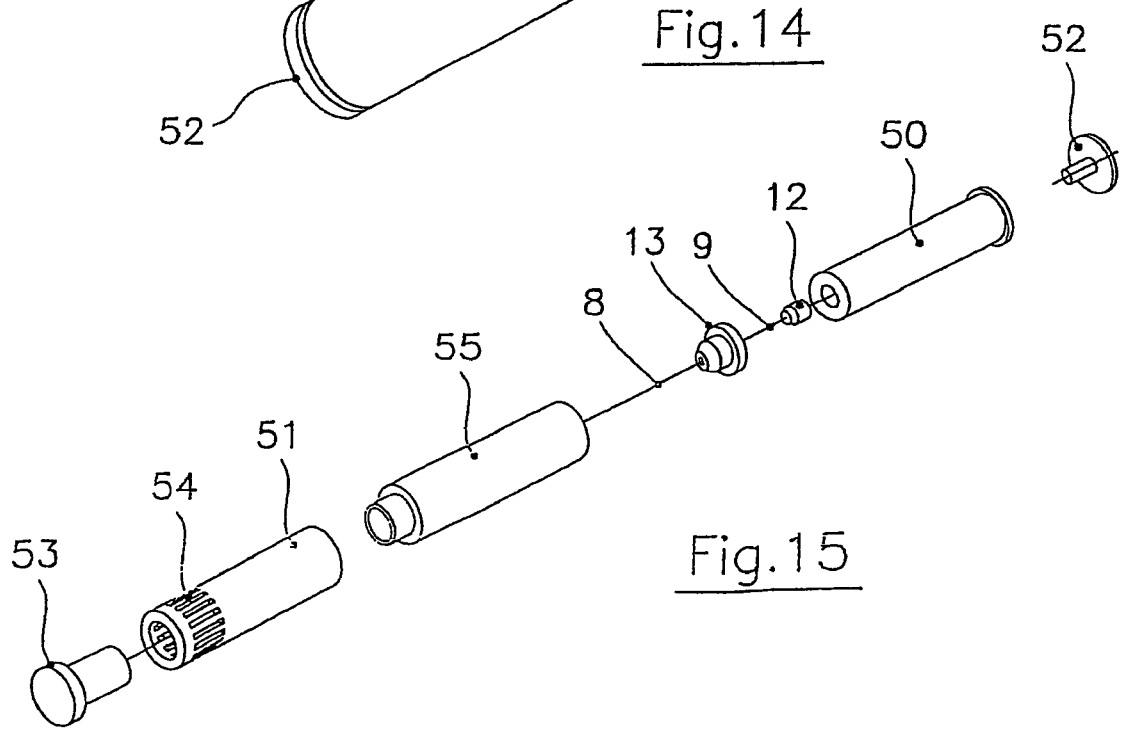
FIG. 15 is an exploded perspective view of the protective container of FIG. 14 with the probe housed therein.

FIGS. 14 and 15 show a protective container for use with the SPME fiber probe and apparatus, according to still another aspect of the present invention, which enables sampling to be done by users in the field without risk of damage to the SPME fiber. This container preferably comprises two cylindrical elements 50 and 55, which surround the fiber and prevent any movement of flange 13 or adaptor cap 12 so as to avoid a change in fiber length Z during sampling. Element 50 engages with the inside of element 55 such that flange 13 rests against the bottom of the latter, and the end of element 50 abuts the flange. Element 55 is engaged partially in a further tubular element 51, which protects the needle during fiber sampling and transport. Element 51 has slits 54 for enabling the fiber to come into contact with a flow of air in the environment being analyzed, without creating a second diffusion chamber (which would misrepresent the value of the sampling range). Caps 52 and 53 are used at the conclusion of sampling procedures in order to interrupt fiber absorption and enable transportation in a safe manner.

In this manner, the apparatus according to the present invention fully achieves the stated objectives. Specifically, it enables full automation of the SPME analytical procedure, both when the gas chromatograph is fed with probes already exposed in other environments, and when the analyte must be extracted from the contents of test tubes accessible to the sampler arm. This reduces drastically the frequency of intervention by the user, thereby minimizing risk of error. In addition, the time necessary to complete the analyses is reduced such that the apparatus can operate continuously for several days without user intervention.

Moreover, full automation of the procedure is achieved by relatively simple structural changes to conventional equipment. In other words, all necessary components can be supplied in the form of a kit for converting a partially-automated apparatus already in use to a fully-automated apparatus, according to the present invention.

Last, a further benefit advantage of the sampling apparatus and the relevant probe, according to the present invention, is their use not only for automatically feeding exposed SPME fibers to a gas chromatographic apparatus, but also performing automatic sampling in an unattended sampling station, e.g., during air analysis, wherein, at a selected time, a probe must be exposed in a sampling window and, after a predetermined time interval, stored back on a rack to be analyzed later at a remote laboratory.

Various modifications and alterations to the invention may be appreciated based on a review of the disclosure. These changes and additions are intended to be within the scope and spirit of the invention as defined by the following claims.

What is claimed is:

1. An automatic solid-phase microextraction apparatus using a probe comprising a fiber arranged slidingly inside a needle such that the fiber can be exposed to an environment from which to absorb an analyte of interest and then inside a gas chromatographic injector for the desorption of the analyte, the apparatus comprising an arm movable according to a pre-established program, with a head carrying a substantially tubular holder with a chamber for the probe and a plunger in the holder for actuating the protrusion and withdrawal of at least a portion of the fiber, the apparatus also comprising a storage unit of test tubes containing samples to analyze and/or probes with already-exposed fibers, wherein:

one end of the fiber in the probe mounts a connection element made of a selected ferromagnetic material and an end of the needle wherein the fiber is engaged has a ferromagnetic flange;

the plunger in the holder has at least one magnet at the end interacting with the fiber, and one or more further magnets provided at a free end of the holder;

the head comprises at least one guide block for slidingly housing the needle when the probe is engaged in the holder, the guide block being arranged underneath the free end of the holder and mounts at least one magnet at its lower end;

there is provided an intermediate transfer bracket accessible to the mobile arm and suitable for vertically supporting one probe, and comprising a device for engaging a ferromagnetic connector on the fiber and the ferromagnetic flange on the needle;

the head of the movable arm being suitable for collecting the probe according to a first collection mode, by bringing the end of the at least one guide block into engagement with the ferromagnetic connector on the fiber, or according to a second collection mode, by bringing the end of the plunger and the free end of the holder respectively into engagement with the connector on the fiber and the flange on the needle, whereby the probe is placed inside the chamber of the holder with the needle extending axially therefrom;

the first collection mode being used to transfer the probe from the storage unit to the intermediate transfer bracket and vice versa, while the second collection mode is used to transfer the probe from the intermediate transfer bracket to the gas chromatograph injector or to the storage unit to absorb an analyte, as a result of corresponding movements of the mobile arm.

2. The apparatus set forth in claim 1, wherein the intermediate transfer bracket comprises an upright with two supporting elements extending therefrom, with respective coaxial seats in which the connection element on the fiber and the flange on the needle are laterally engaged, each of the seats having a radial discontinuity suitable for the passage of the fiber and the needle, respectively.

3. The apparatus set forth in claim 2, wherein a pair of parallel arms extend from the upright between the supporting elements the arms being intended for abutting on the flange of the needle so as to exert a force thereon that exceeds the magnetic force of attraction exerted by the magnet on the free end of the holder when the head is raised after the magnetic end of the plunger has been separated from the connection element on the fiber.

4. The apparatus set forth in claim 1, wherein the flange of the needle has a lateral radial slit and wherein a reference tooth is provided on a respective supporting element of the intermediate transfer bracket, on which a seat for the flange is formed, that engages in the slit, in the first collection mode the at least one guide block being separated from the connection element by the head moving orthogonally away from the probe.

5. The apparatus set forth in claim 1, wherein the connection element, to which an adaptor cap made of a selected ferromagnetic material is attached, is constructed of a polymeric material.

6. The apparatus set forth in claim 1, wherein the ferromagnetic flange on the needle is secured to a spacer ring at the end of the needle by a mounting sleeve coaxial to the needle.

7. The apparatus set forth in claim 6, wherein the flange has a lateral radial discontinuity to allow for passage of the needle.

8. The apparatus set forth in claim 1, further comprising a device for adjusting the degree to which the fiber is withdrawn inside the needle, the device including a support plate, a first block secured to the plate with a seat for retaining the connection element of the fiber and a second block sliding along the support plate with a seat for retaining the flange on the needle, the support plate having a graduated scale along the axis in which the second block slides for adjusting the extent of the fiber's withdrawal to a pre-established value when the probe is placed on the blocks.

9. The apparatus set forth in claim 1, further comprising a protective container for the probe, that includes a first tubular element for containing the portion of the fiber extending from the flange, a second tubular element in which the first tubular element engages so as to bring the flange into engagement with a bottom of the second tubular member, and a third tubular element in which the second tubular element at least partially engages such that the needle extends inside the third tubular element, slits being formed on the third tubular element to place its interior in communication with the outside environment containing the substance being adsorbed on the fiber.

10. The apparatus set forth in claim 1, further comprising fibers, yet to be exposed, that are accessible to the movable arm.

11. A probe for solid-phase microextraction, the probe comprising a fiber slidingly housed in a needle, wherein the fiber has a connector made of a selected ferromagnetic material at one end, and an end of the needle in which the fiber is engaged has a flange made of selected ferromagnetic material.

12. The probe set forth in claim 11, wherein the connector on the fiber includes a plastic connector attached to one end of the fiber and an adaptor cap made of a selected ferromagnetic material attached to the connector.

13. The probe set forth in claim 11, wherein the ferromagnetic flange on the needle is attached to a spacer ring at the end of the needle by a sleeve coaxial thereto.

14. The probe set forth in claim 11, wherein the flange has a lateral radial discontinuity to allow for the passage of the needle.

15. The probe set forth in claim 14, wherein the lateral radial discontinuity has a widened opening section.

16. An adapter for converting semiautomatic solid-phase microextraction sampling equipment to equipment that is fully automatic, using a probe comprising a fiber slidingly housed in a needle so that the fiber can be exposed in an environment, from which it can absorb an analyte of interest, and in a gas chromatograph injector for desorption of the analyte, the adaptor comprising:

an adaptor cap made of a selected ferromagnetic material for attaching to a connector situated at an end of the fiber, the connector being made of a selected ferromagnetic material;

a flange made of a selected ferromagnetic material with a corresponding mounting sleeve for attaching to a spacer ring on an end of the needle;

a plurality of magnetic elements for attaching to the end of a plunger of a holder for the probe, to a free end of the holder, and to a free end of a guide block for slidingly housing the needle carried by a head of the mobile arm forming part of the equipment; and an intermediate transfer bracket for vertically supporting a probe and comprising a device for engaging the ferromagnetic connector on the fiber and the ferromagnetic flange.

* * * * *